United States Patent [19]
D'Amelio, Sr. et al.

[11] Patent Number: 5,973,005
[45] Date of Patent: Oct. 26, 1999

[54] AQUEOUS CREATINE SOLUTION AND PROCESS OF PRODUCING A STABLE, BIOAVAILABLE AQUEOUS CREATINE SOLUTION

[75] Inventors: Frank S. D'Amelio, Sr., Huntington; Youssef W. Mirhom, Huntington Station, both of N.Y.

[73] Assignee: Bio-Bontanica, Inc., Hauppauge, N.Y.

[21] Appl. No.: 09/031,290

[22] Filed: Feb. 26, 1998

[51] Int. Cl.[6] .................................................. A61K 31/195
[52] U.S. Cl. ........................................... 514/565; 562/560
[58] Field of Search .............................. 514/565; 562/560

[56] References Cited

U.S. PATENT DOCUMENTS

| | | | |
|---|---|---|---|
| 5,091,404 | 2/1992 | Elgebaly | 514/401 |
| 5,612,375 | 3/1997 | Sueoka | 514/565 |
| 5,627,172 | 5/1997 | Almada et al. | 514/120 |
| 5,686,588 | 11/1997 | Yoo et al. | 536/13.3 |

FOREIGN PATENT DOCUMENTS

| | | | |
|---|---|---|---|
| 9402127 | 2/1994 | WIPO | A61K 31/195 |

OTHER PUBLICATIONS

Martindale, The Extra Pharmacopoeia, The Pharmaceutical Press 1982, Anhydrous Sodium Phosphate/Proprietary Preparations of Some Other Electrolyte Solutions, p. 643.

Creatine Phosphate Research Underway, *http://ussa–sport.ussa.edu/pubs/creatin.num,* Feb. 5, 1997.

Edgar et al., The Equilibrium Between Creatine and Creatinine, in Aqueous Solution. The Effect of Hydrogen Ion, J. Am. Chem. Soc., vol. 47, pp. 1179–1188, Apr. 4, 1925.

Dhar et al, Chem. Abstracts, vol. 56, #9702h, 1961.

Dhar et al, Chem. Abstracts, vol. 56, #9703a, 1961.

*Primary Examiner*—James H. Reamer
*Attorney, Agent, or Firm*—Roylance, Abrams, Berdo & Goodman, L.L.P.

[57] ABSTRACT

A stable aqueous solution of creatine acid sulfate provides a source of creatine to an animal when taken orally. The aqueous solution of creatine acid sulfate (after neutralization and buffering) has a pH of about 7.2 to about 7.8 and is stable for at least six months at room temperature. The creatine acid sulfate is produced by adding creatine monohydrate to a sulfuric acid solution in a stoichiometric amount to result in creatine acid sulfate having a pH initially of 2.0–3.0. The resulting creatine acid sulfate is diluted with water and neutralized to raise the pH and avoid the formation of creatinine. The resulting creatine acid sulfate solution preferably contains a buffering and neutralizing agent such as tribasic potassium phosphate which forms mono- and dibasic potassium phosphates by interaction with the hydrogen ions liberated from the acid sulfate. The aqueous solution can be combined with a sweetener, electrolyte and carbohydrate source to produce a stable drink for providing a source of creatine to an animal in need thereof. An effective amount of glycerol is preferably added to enhance absorption of the creatine through the intestinal wall into the bloodstream and eventually to the needy skeletal muscles.

38 Claims, 2 Drawing Sheets

AQUEOUS CREATINE SOLUTION AND PROCESS OF PRODUCING A STABLE, BIOAVAILABLE AQUEOUS CREATINE SOLUTION

FIELD OF THE INVENTION

The present invention is directed to an aqueous solution of a creatine source and to a process of supplying a creatine source to an animal. More particularly, the invention is directed to a stable creatine solution in a readily bioavailable form. The invention is further directed to a process of producing a soluble creatine form by combining a calculated amount of suitably diluted sulfuric acid to creatine monohydrate.

BACKGROUND OF THE INVENTION

It is well established that the energy which enables the muscles in mammals to contract and expand is produced from adenosine triphosphate (ATP). The adenosine triphosphate metabolizes in the muscle by cleaving a phosphate radical to release the energy to contract the muscle and to produce adenosine diphosphate (ADP) as a byproduct. As the amount of adenosine triphosphate is depleted during extended exercise, muscle strength decreases and muscle fatigue increases.

Adenosine triphosphate can be produced in the muscle from glycogen or creatine phosphate. Creatine phosphate provides a ready source of phosphate and is able to resynthesize adenosine triphosphate at nearly twice the rate compared to glycogen. The amount of creatine phosphate in the muscle and the bloodstream are important in the time required to recover from muscle fatigue.

Creatine is produced naturally in humans and other animals and is converted to creatine phosphate in the muscles. The creatine phosphate is stored in the muscle as an available source of phosphate for the resynthesis of adenosine triphosphate from adenosine diphosphate.

Creatine is produced in the liver, kidney and pancreas and is supplied to the body by the food intake. Creatine is only sparingly soluble in water and is normally present in the bloodstream at a concentration of about 50 $\mu$mol per liter of blood. The creatine enters the muscle tissue by active transport where it is converted to creatine phosphate. Muscle fatigue and the accumulation of lactic acid occur when the supply of creatine phosphate is exhausted and the adenosine diphosphate cannot be converted to adenosine triphosphate.

Numerous efforts have been made to increase the content of the creatine phosphate in the muscle to increase the muscle power and the ability to exercise longer. Creatine can be supplied to the body to enhance physical performance since the list of drugs prohibited by the International Olympic Committee, which includes more than 120 kinds, does not include creatine, which is an amino acid normally biosynthesized in vertebrates. For example, International Patent Publication No. WO 94/02127 discloses a method of increasing the creatine levels in the body by administering creatine orally, enterally or parenterally to an animal. However, creatine is generally not effectively administered orally in powder form since creatine rapidly converts to creatinine by the acidic conditions in the stomach, and is not in a soluble bioavailable form causing a disturbance in the positive osmotic pressure necessary for absorption. Creatinine is the inactive form of creatine which is quickly depleted from the body. Creatinine is not able to convert to creatine phosphate and does not participate in the regeneration of adenosine triphosphate and is excreted in the urine.

Creatine has also been used in aqueous solutions as a beverage which is intended to supply creatine to the body. Examples of beverages containing solubilized creatine are disclosed in U.S. Pat. Nos. 5,612,375 and 5,397,786. Other methods which do not use any heat have to be developed since heat was found to accelerate the conversion of creatine to creatinine. Creatine is only sparingly soluble in water so that the amount of creatine that can be supplied in solution is limited. In addition, acidic conditions in the stomach convert the creatine to creatinine, thereby reducing the amount of creatine available for absorption by the body. Heat and hydrogen ion concentration accelerate decomposition of creatine.

Accordingly, a continuing need exists in the industry and in athletic circles for an improved method of administering creatine and supplying creatine to the body in stable form.

SUMMARY OF THE INVENTION

The present invention is directed to a method of supplying creatine to an animal, and particularly humans, in a soluble, stable form that can be utilized and absorbed by the body. More particularly, the invention is directed to a creatine solution and to a process of producing a soluble form of creatine acid sulfate as the starting material.

The solubilizing agent is a specific dilution of sulfuric acid in a precalculated amount. Sulfuric acid is selected for several reasons, including its solubilizing property for creatine and low toxicity of the sulfate ion. Sulfate salts have even been used to hasten the excretion of drugs in overdosage and other toxic substances by i.v.i.

Another object of the invention is to provide a method of producing an aqueous solution of creatine with diluted sulfuric acid and dispensing the solution in a form that can be readily utilized and absorbed by the body to provide a source of creatine when administered orally.

A further object of the invention is to provide a method of producing an aqueous solution of a creatine acid sulfate salt in a form that is stable for extended periods of time.

Another object of the invention is to provide a method of introducing a source of creatine to an animal in a form that is readily water soluble.

Another object of the invention is to provide a buffered aqueous solution of creatine acid sulfate salt that is stable for extended periods of time.

Still another object of the invention is to provide a source of phosphate ion with a creatine source to increase the effect of creatine loading.

The objects of the invention are basically attained by providing a process of producing a creatine acid sulfate salt solution. The soluble form of creatine is produced by forming an aqueous solution of sulfuric acid and combining with a calculated amount of creatine monohydrate whereby the acid reacts with the creatine. The resulting reaction product is a paste-like substance of the acid sulfate salt of creatine with a pH of about 2.00 to about 3.00. The paste is then diluted with water to form a solution and to disperse the creatine acid sulfate. A special buffering agent can be added to a solution of the product to bring the pH near neutral, and preferably a slightly alkaline pH of about 7.20 to about 7.8. A suitable buffering agent can be, for example, tribasic potassium phosphate, which reacts with the H$^+$ions liberated in solution from the acid sulfate salt to form a suitable mixture of mono-, di-, and tribasic phosphates of the required buffered pH.

The objects of the invention are further attained by providing a stable aqueous solution of a creatine acid sulfate salt having a buffering agent and a pH of about 7.5. The buffering and neutralizing agent can be, for example, tribasic potassium phosphate. The aqueous solution can be in the form of a drink or beverage to be consumed orally by an animal to supply creatine in a stable form that is readily absorbed by the body. The beverage can further include a sweetener, a source of electrolytes, a source of carbohydrates and a phosphate source to provide a phosphate for the synthesis of creatine phosphate. A suitable amount of glycerol is preferably added as an osmotic absorption enhancer for ready bioavailability.

These and other objects, advantages and salient features of the invention will become apparent from the following detailed description and the annexed drawings which form a part of this original disclosure.

BRIEF DESCRIPTION OF THE DRAWINGS

Referring to the drawings which form a part of this disclosure in which.

DETAILED DESCRIPTION OF THE INVENTION

Figure 1:
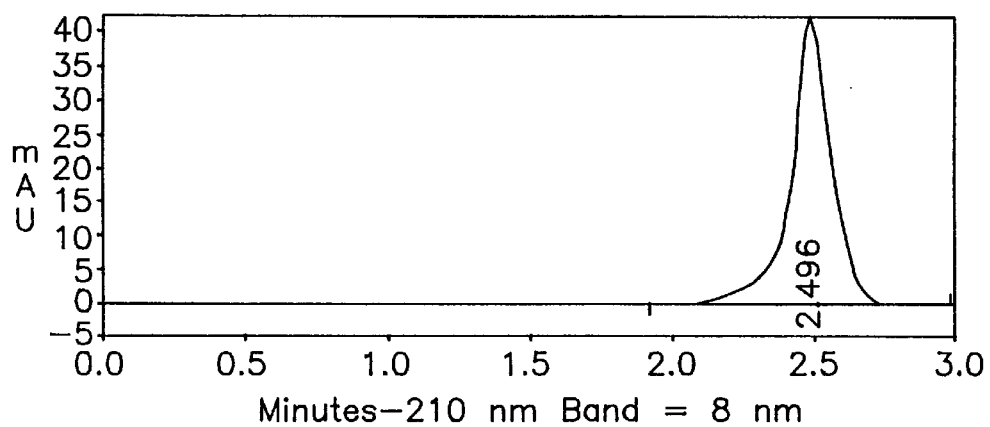
FIG. 1 is a high pressure liquid chromatography (HPLC) chromatogram of creatine monohydrate dissolved in water (fresh dilute solution) showing a single peak for creatine monohydrate at 2.496.

The present invention is directed to a process of producing a stable solution of creatine acid sulfate salt and to a shelf stable beverage containing creatine. The solution is obtained by solubilizing creatine in the form of an acid sulfate salt. The invention is further directed to a process of supplying an animal with a stable, bioavailable source of creatine.

Creatine, N-(aminoiminomethyl)-N-methylglycine, is present in the muscle tissues of vertebrates and can be commercially isolated from meat extracts. A large portion of creatine found in muscle tissue is combined with phosphoric acid in the form of phosphocreatine (creatine phosphate). Creatine is normally produced in the liver and kidneys by the transfer of the guanidine moiety of arginine to glycine which is then methylated to give creatine. Creatine has the formula:

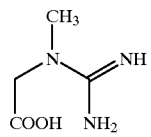

Creatine is moderately soluble in water such that 1 gram of creatine dissolves in about 75 grams of water. In aqueous solutions, creatine converts to creatinine. Aqueous and alkaline solutions contain an equilibrium mixture of creatine and creatinine. Under acidic conditions, the formation of creatinine from free creatine is complete. Creatinine has the formula

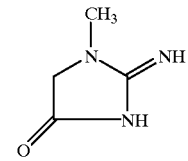

Creatine in solid form is commercially available as creatine monohydrate which has a monoclinic form having one molecule of water. Anhydrous creatine is produced by heating creatine monohydrate to about 100° C. Creatine combines with phosphoric acid in the body to form phosphocreatine which has the formula:

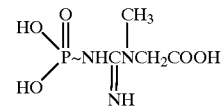

The present invention is directed to a process of supplying creatine in a form that is available for absorption by the body to replace the creatine consumed during exercise or other muscle activity. Creatine is converted to creatine phosphate by the creatine kinase enzyme. The creatine phosphate transfers its phosphate to adenosine diphosphate during the regeneration of adenosine triphosphate. The rate of resynthesis of adenosine triphosphate increases as the amount of creatine phosphate and creatine in the muscles increases. The present invention is, therefore, directed to a process of supplying a source of creatine to the body and particularly to the muscles to increase stamina, reduce the onset of muscle fatigue and to provide a rapid recovery from muscle fatigue.

The composition of the invention is important in disease or age-related creatine deficiencies in the brain and skeletal muscle. Creatine supplementation helps rebuild muscle mass permitting inactive or dystrophic muscle to work harder during therapy and thus, rebuild itself to its normal state. It thus can provide more energy to older, less active individuals.

In a preferred embodiment of the invention, a creatine salt is formed to provide a readily water soluble and stable form of a creatine compound that can be used to resupply the body after exercise. In preferred embodiments, the creatine salt is an acid sulfate salt.

The creatine acid sulfate salt in preferred embodiments is produced as an aqueous paste. The creatine sulfate salt is produced by reacting creatine monohydrate with a previously calculated amount of sulfuric acid in an aqueous solution. The concentration of the sulfuric acid is preferably sufficiently dilute to provide sufficient water for the sulfuric acid and prevent conversion of creatine to creatinine by withdrawal of water from the molecule.

Creatine normally converts to creatinine when left in an acidic aqueous medium. Therefore, creatine monohydrate is added to the dilute sulfuric acid followed rapidly by further dilution and neutralization. In preferred embodiments, the resulting solution is diluted immediately after the creatine monohydrate is added to the dilute sulfuric acid and the reaction is complete. The resulting creatine acid sulfate reaction product is diluted with distilled water in a ratio of about 1:20 to about 1:25 by volume. The creatine acid sulfate salt formed by the reaction of creatine monohydrate and the sulfuric acid has a pH of about 2.0 to about 3.0. Preferably, the reaction product is immediately diluted with distilled water and quickly neutralized to inhibit the formation of creatinine. In a preferred form of the invention, the sulfuric acid solution which is combined with the creatine monohydrate has a concentration of about 31% to about 35% by weight of $H_2SO_4$.

The creatine can be a commercially available form which typically is the creatine monohydrate. Creatine monohydrate is available from several commercial sources. The amount of creatine combined with the sulfuric acid is preferably a calculated amount corresponding to about 1.0 mole of sulfuric acid for every 2 moles of anhydrous creatine and so that the resulting aqueous solution of the acid creatine sulfate after dilution has a pH of 2.0–3.0 and the sulfuric acid reacts with the creatine to form a soluble acid sulfate salt. Preferably, substantially all of the creatine monohydrate is converted to a soluble acid sulfate form so that substantially no creatine remains which would otherwise be converted to creatinine in solution.

In the preparation of the creatine acid sulfate salt, the concentration of the sulfuric acid solution is first determined, which is preferably between 31% and 35% sulfuric acid. Then the amount of creatine monohydrate is calculated to provide a molar ratio of creatine to sulfuric acid to be about 2.0:1.0. The amount of creatine monohydrate is then determined from the calculated amount of the anhydrous creatine. Creatine monohydrate is generally preferred since anhydrous creatine can be more easily converted to creatinine than the monohydrate.

The sulfuric acid solution is preferably prepared from concentrated sulfuric acid, such as 96% by weight sulfuric acid. The concentrated sulfuric acid is diluted with distilled water to the desired concentration which typically has a pH of at least 1.0.

The soluble creatine acid sulfate salt is preferably produced at room temperature while cooling. Preferably, the creatine monohydrate in a dry, crystalline form is added directly to the sulfuric acid solution with continuous mixing at room temperature while cooling. It is not desirable to combine the creatine monohydrate with concentrated sulfuric acid as it is converted easily to creatinine under such condition. The concentration of the sulfuric acid solution is preferably less than about 35% by weight sulfuric acid to inhibit the conversion of the creatine to creatinine and not less than 31% by weight to bring the reaction to completion.

The creatine acid sulfate salt is generally produced as a paste which can be used to form an aqueous solution having a pH of 2.0–3.0 after dilution with water. In further embodiments a pH adjusting and buffering agent can be added to the resulting solution to selectively adjust the pH to 7.2–7.8 to stabilize the creatine acid sulfate. A suitable pH adjusting and buffering agent can be, for example, tribasic potassium phosphate which will at the same time act as a buffer, together with other phosphate salts formed, to stabilize the creatine acid sulfate.

The creatine solution preferably includes at least one buffering agent to maintain the pH in the range of about 7.2 to about 7.8. A preferred buffering agent is tribasic potassium phosphate. The addition of tribasic potassium phosphate to the solution forms a buffer system with the hydrogen ions liberated from the creatine acid sulfate salt in solution. Tribasic potassium phosphate is a preferred buffering agent since it is able to bring the pH to the desired level and effectively buffer the solution while providing a source of phosphate for the formation of creatine phosphate in the muscles. The tribasic potassium phosphate can be added as a solid or powder to the diluted creatine acid sulfate solution. Preferably, the tribasic potassium phosphate is added as an aqueous solution having a pH of about 12.0.

The resulting creatine solution, thus prepared, is stable at room temperature for extended periods of time. The solution obtained comprises substantially pure creatine with no detectable amounts of creatinine. Stability tests have demonstrated that this solution of creatine is stable at room temperature for at least about six months. High Performance Liquid Chromatography (HPLC) chromatograms show substantially pure creatine acid sulfate being produced with undetectable amounts of creatinine or other impurities.

In a further embodiment of the invention a beverage is produced which can be consumed by an animal, and particularly humans, to provide a convenient and effective source of creatine. The beverage contains an effective amount of a creatine salt to replenish the body with creatine. The beverage provides a stabilized source of a creatine salt which can be absorbed by the body to increase the amount of creatine in the bloodstream and the muscles.

The beverage containing the creatine salt starting with the preparation of creatine acid sulfate is produced according to the method of the previous embodiment by forming a dilute aqueous solution of sulfuric acid and adding an amount of creatine monohydrate to react with the sulfuric acid and to produce a paste of substantially pure creatine acid sulfate substantially in the absence of creatinine. The resulting paste is then diluted with water to obtain a solution having the equivalent of about 0.5 to about 4.0 grams, preferably about 1.0 to 3.0 grams and most preferably about 1.0 to 1.5 grams of creatine acid sulfate per 100 ml of the beverage. Typically, the beverage contains the equivalent of about 1.37% to about 2.06% by weight creatine acid sulfate. An adult human consuming about 600 ml of this solution is found to obtain a maximum creatine concentration in the bloodstream of about 800 mmol/l in about one hour.

A buffering and neutralizing agent is then added to the solution to maintain the pH preferably from about 7.2 to about 7.8. In preferred embodiments, the buffering and neutralizing agent is tribasic potassium phosphate which can be added in an amount of about 1 part to about 2 parts by weight based on the calculated weight of the creatine in the solution. The tribasic potassium phosphate can be added in the form of an aqueous solution having a pH of about 12.0.

The beverage can contain additional components to provide the desired nutrients, electrolytes, and flavor. Suitable sweeteners such as glycerol, sorbitol, sucrose, fructose, maltose, dextrose, aspartame, cyclamates and stevia can be added in an amount to provide the desired sweeteners. Carbohydrates, which are typically sugars, can be added in a desired amount. Preservatives such as sodium benzoate, methylparaben and propylparaben can be added in an effective amount to increase the shelf life of the solution. Suitable flavoring agents, such as natural or synthetic fruit flavors, can also be added. Preferably, the beverage contains at least one source of phosphate that can be taken up by the body.

The addition of a suitable amount of glycerol is preferable. It has been found that glycerol acts as an osmotic carrier of creatine through the intestinal wall and into the bloodstream. The prior creatine powder or suspensions usually lead to withdrawal of water from the intestinal wall and hinder absorption by reverse osmosis. The creatine acid sulfate of the invention avoids these problems. Preferably, the solution contains about 8.0% to about 10.0% by weight glycerol.

In preferred embodiments, the buffering agent is tribasic potassium phosphate to provide a potassium source and a phosphate source to the beverage. As it was found that phosphate loading can enhance performance. The tribasic potassium phosphate provides a source of phosphate which can be taken up by the body for use in the production of creatine phosphate. It is believed that loading both creatine and phosphate at the same time can induce a potentiating effect and not merely a simple additive effect. The creatine acid sulfate also provides a source of creatine in a form which can be taken up by the body. The absorption of the phosphate and creatine by the body provides the necessary components for the synthesis of phosphocreatine. The beverage is effective in preserving and supplying creatine in the body to enhance muscular activity, reduce fatigue and reduce the recovery time after exercise. In further embodiments, an amount of potassium hydroxide can be added to adjust the pH as considered necessary.

Other additives can be included in the beverage to supply various nutrients. Examples of suitable nutrients include, amino acids, minerals, such as calcium and magnesium, vitamins, proteins, protein hydrolysates, and the like. An example of a suitable beverage contains the equivalent of about 1.37% to about 2.06% creatine acid sulfate, about 1.0% to about 2.0% tribasic potassium phosphate, about 8.0% to about 10.0% glycerol, about 15% to about 20% sorbitol, about 0.10% sodium benzoate and the balance water, wherein the percentages are by weight. If desired, the beverage can be sterilized, adopting any suitable method which does not effect the stability of creatine.

In further embodiments, the beverage contains glutamine and pyruvic acid, pyruvate salts and mixtures thereof, to provide an additional energy source. The beverage can further contain an amino acid selected from the group consisting of glycine, arginine, methionine and mixtures thereof, to provide a source of the metabolic precursors of creatine.

The beverage produced according to the invention supplies creatine in a form which attains maximum plasma concentration in about one hour after ingestion. In embodiments, 600 ml of the beverage containing the equivalent of about 6 grams of creatine produces a creatine concentration of about 800 mmol per liter of blood in about one hour.

The following Examples demonstrate preferred embodiments of the invention.

EXAMPLE 1

An aqueous solution of creatine was prepared by dissolving 0.05 mg/ml of 99% pure creatine monohydrate in distilled water. This concentration corresponds to about 0.044 mg/ml of anhydrous creatine. A 1 ml sample was analyzed by HPLC using a Shimadzu LC-10AD Liquid Chromatograph. The operating parameters are as follows:

|  | Sample Amount | ISTD Amount | Mult. Factor |
| --- | --- | --- | --- |
| Calibration: | 1.000 | 1.000 | 1.000 |
| Run: | 1.000 | 1.000 | 1.000 |
| Channel A Results - PDA Channel 1,210 nm, 8 nm Band | | | |

| Peak # | RT | Area | Area # | Height |
| --- | --- | --- | --- | --- |
| — | 0.470 | 0 | 0.00 | 0 |
| 1 | 2.496 | 440793 | 100.00 | 42804 |
| Totals: | | 440793 | 100.00 | 42804 |

The resulting chromatogram shown in FIG. 1 produced a single peak at 2.496 indicating the sample contained substantially pure creatine with substantially no creatinine or other impurities.

EXAMPLE 2

An aqueous sample of creatinine was prepared by dissolving 0.04 mg/ml of creatinine in distilled water. A 1.0 ml sample was analyzed using HPLC Chromatography as in Example 1. The operating parameters are as follows:

|  | Sample Amount | ISTD Amount | Mult. Factor |
| --- | --- | --- | --- |
| Calibration: | 1.000 | 1.000 | 1.000 |
| Run: | 1.000 | 1.000 | 1.000 |
| Channel A Results - PDA Channel 1,210 nm, 8 nm Band | | | |

| Peak # | RT | Area | Area % | Height |
| --- | --- | --- | --- | --- |
| — | 0.470 | 0 | 0.00 | 0 |
| 1 | 2.219 | 1206169 | 100.00 | 127332 |
| Totals: | | 1206169 | 100.00 | 127332 |

Figure 2:
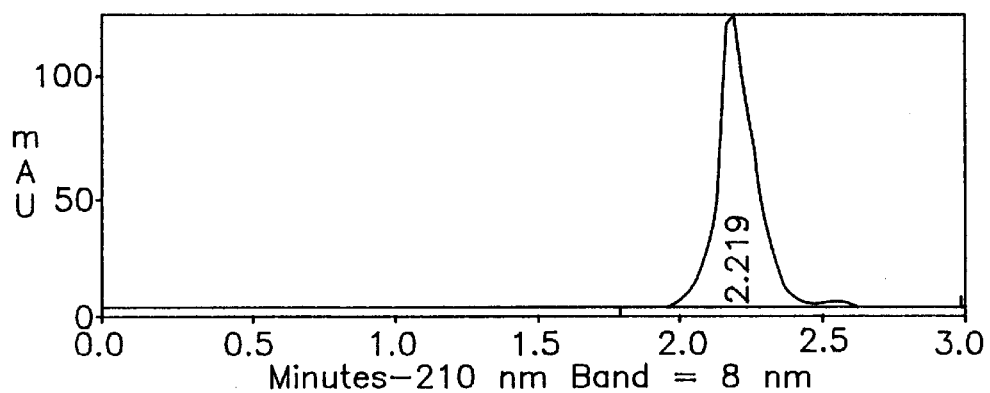
FIG. 2 is an HPLC chromatogram of an aqueous solution of a commercially available creatinine showing a single peak for creatinine at 2.219.

The HPLC Chromatogram as shown in FIG. 2 displays a single peak at 2.219 corresponding to the creatinine.

EXAMPLE 3

An aqueous solution of creatine acid sulfate was prepared according to the present invention. A sulfuric acid solution was prepared by diluting 0.39 grams of concentrated (96%) sulfuric acid in 0.8 grams of distilled water. The resulting solution contained about 31% sulfuric acid. Creatine monohydrate (99%) was added at room temperature while cooling to the sulfuric acid solution in an amount of 1.15 grams which corresponds to about 1.0 gram of anhydrous creatine to produce the creatine acid sulfate. The creatine acid sulfate produced is freely soluble in water with no visible impurities or precipitates, giving a crystal clear solution.

A 1 ml sample of the resulting creatine acid sulfate was suitably diluted and analyzed using HPLC Chromatography as in Example 1. The operating parameters are as follows:

|  | Sample Amount | ISTD Amount | Mult. Factor |
| --- | --- | --- | --- |
| Calibration: | 1.000 | 1.000 | 1.000 |
| Run: | 1.000 | 1.000 | 1.000 |
| Channel A Results - PDA Channel 1,210 nm, 8 nm Band | | | |

| Peak # | RT | Area | Area % | Height |
| --- | --- | --- | --- | --- |
| — | 0.470 | 0 | 0.00 | 0 |
| 1 | 2.645 | 2192187 | 100.00 | 211582 |
| Totals: | | 2192187 | 100.00 | 211582 |

Figure 3:
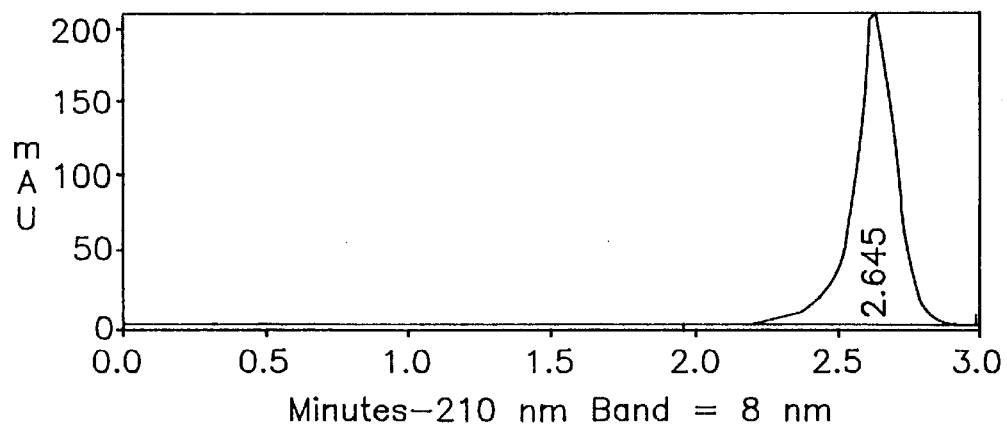
FIG. 3 is an HPLC chromatogram of an aqueous solution of creatine acid sulfate salt produced according to the present invention showing substantially pure creatine peak with substantially no creatinine being formed.

The resulting chromatogram shown in FIG. 3 displays a single peak at 2.645 indicating the sample contains substantially pure creatine acid sulfate with essentially no creatinine or other impurities being present. The slight variation in retention time is due to the sensitivity of HPLC methods to slight variations in pH values.

EXAMPLE 4

Figure 4:
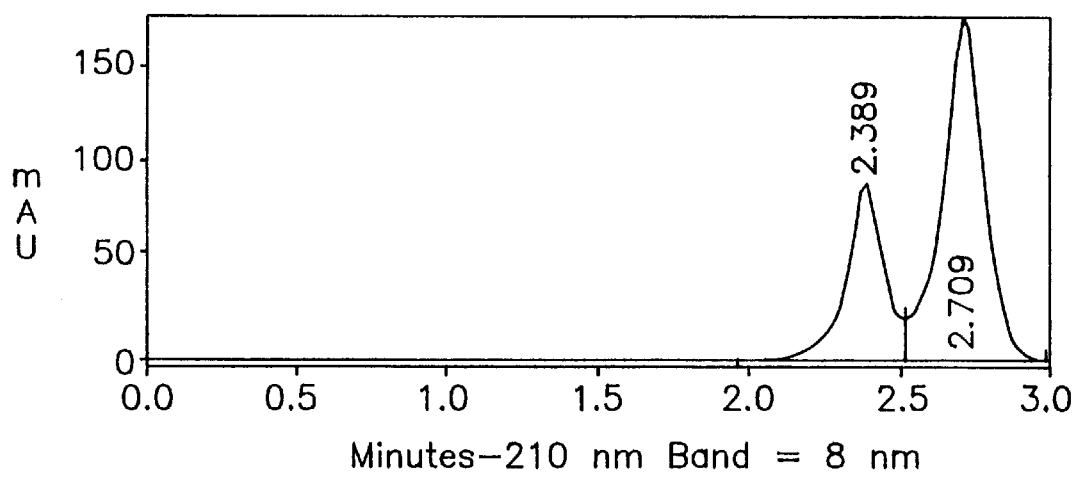
FIG. 4 is an HPLC chromatogram of an aqueous solution prepared by dissolving commercially obtained creatine in warm, slightly alkaline water showing that the resulting solution contains about 15% creatinine and about 85% creatine.

A creatine solution was prepared by forming a weak alkaline aqueous solution and heating to about 80° C. 1.0 gram of creatine monohydrate was added to the heated alkaline solution and stirred to dissolve the creatine. The solution was analyzed by HPLC Chromatography as in Example 1 to obtain the chromatogram of FIG. 4. The operating parameters were as follows:

|  | Sample Amount | ISTD Amount | Mult. Factor |
| --- | --- | --- | --- |
| Calibration: | 1.000 | 1.000 | 1.000 |
| Run: | 1.000 | 1.000 | 1.000 |

Channel A Results - PDA Channel 1,210 nm, 8 nm Band

| Peak # | RT | Area | Area % | Height |
| --- | --- | --- | --- | --- |
| — | 0.470 | 0 | 0.00 | 0 |
| 1 | 2.389 | 826536 | 32.27 | 93439 |
| 2 | 2.709 | 1735052 | 67.73 | 177002 |
| Totals: |  | 2561588 | 100.00 | 270441 |

The chromatogram shows a peak at 2.709 representing the creatine and a peak at 2.389 representing about 15% creatinine is produced. (The pH affects the retention time as explained above.)

EXAMPLE 5

A beverage for supplying creatine in a stable solution was prepared from 2.34 g of the creatine acid sulfate obtained by the process of Example 3, corresponding to 1.0 g of anhydrous creatine. The creatine acid sulfate was diluted with about 40 ml of distilled water. To the resulting solution was added 1.12 g of tribasic potassium phosphate, 8.33 g of glycerol (99%), 16.66 g of sorbitol (70%) and 0.10 g of sodium benzoate. The resulting solution had almost neutral pH, clear and colorless, with a sweet, agreeable taste.

The creatine acid sulfate was completely soluble in the solution and was stable for at least six months. An adult consuming 600 ml of the solution produced a maximum creatine concentration in the blood of about 800 mmol/l in about one hour after ingestion.

While advantageous embodiments have been chosen to illustrate the invention, it will be understood by those skilled in the art that various changes and modifications can be made therein without departing from the spirit and scope of the invention as defined in the appended claims.

What is claimed is:

1. A process of producing a creatine acid sulfate solution comprising the steps of forming an aqueous solution of sulfuric acid; and combining creatine monohydrate with said sulfuric acid solution to form a creatine acid sulfate reaction product having a pH of about 2–3, and thereafter immediately diluting and neutralizing said reaction product to avoid the formation of creatinine to form an aqueous solution of creatine acid sulfate.

2. The process of claim 1, wherein said creatine monohydrate is added in a stoichiometric amount to said sulfuric acid solution to produce said creatine acid sulfate substantially in the absence of creatinine.

3. The process of claim 1, wherein said creatine monohydrate is combined with said sulfuric acid in an amount to provide a creatine monohydrate to sulfuric acid in a molar ratio of about 2.0:1.0.

4. The process of claim 2, wherein said resulting creatine acid sulfate in aqueous solution has a pH of less than about 7.8.

5. The process of claim 2, wherein said aqueous solution of creatine acid sulfate has a pH of about 7.2 to about 7.8.

6. The process of claim 1, wherein said aqueous solution of sulfuric acid has a sulfuric acid concentration of about 31% to about 35% by weight.

7. The process of claim 1, further comprising the step of adding a buffering and neutralizing agent to said aqueous creatine acid sulfate solution.

8. The process of claim 7, wherein said buffering and neutralizing agent is tribasic potassium phosphate.

9. The process of claim 7, wherein said buffering and neutralizing agent is a tribasic potassium phosphate solution having a pH of about 12.0.

10. A stable creatine acid sulfate solution comprising an aqueous solution of creatine acid sulfate and a buffering and neutralizing agent, wherein said solution has a pH of less than about 7.8.

11. The creatine acid sulfate solution of claim 10, wherein said buffering and neutralizing agent is tribasic potassium phosphate.

12. The creatine acid sulfate solution of claim 11, wherein said creatine acid sulfate solution has a pH of about 7.2 to about 7.8.

13. The creatine acid sulfate solution of claim 11, further comprising potassium hydroxide in an amount to adjust the pH of said solution to about 7.2 to about 7.8.

14. The creatine acid sulfate solution of claim 10, wherein said creatine acid sulfate is produced by the process of forming an aqueous solution containing about 31% to about 35% by weight sulfuric acid, and adding a creatine source to said solution in an amount with respect to said sulfuric acid to produce a substantially pure creatine acid sulfate at a pH of about 2–3, and immediately thereafter diluting and neutralizing said solution to inhibit the formation of creatinine and to form an aqueous solution of creatine acid sulfate.

15. The creatine acid sulfate solution of claim 14, wherein said creatine source is creatine monohydrate.

16. The creatine acid sulfate solution of claim 12, wherein said creatine source is added to said sulfuric acid solution in an amount to provide a creatine to sulfuric acid in a molar ratio of about 2.0:1.0.

17. An aqueous composition for providing a source of creatine to an animal, said composition comprising an aqueous solution of creatine acid sulfate, and a buffering and neutralizing agent, wherein said composition has a pH of less than about 7.8, is substantially free of creatinine, and is stable at room temperature for at least about 6 months.

18. The composition of claim 17, wherein said composition has a pH of about 7.2 to about 7.8.

19. The composition of claim 17, wherein said buffering and neutralizing agent comprises tribasic potassium phosphate.

20. The composition of claim 17, further comprising glycerol in an amount to provide an osmotic carrier for absorption of creatine through the intestinal wall and into the bloodstream.

21. The composition of claim 17, further comprising a sweetener.

22. The composition of claim 21, wherein said sweetener is sorbitol.

23. The composition of claim 17, comprising the equivalent of about 1.37 to 2.06% creatine acid sulfate, 1.0 to about 2.0% tribasic potassium phosphate, 8.0 to 10.0% glycerol, 15% to 20% sorbitol, 0.1% sodium benzoate and the balance water, wherein said percentages are by weight.

24. The composition of claim 17, further comprising at least one compound selected from the group consisting of pyruvic acid, pyruvate salts, and mixtures thereof.

25. The composition of claim 17, further comprising at least one compound selected from the group consisting of glycine, arginine, methionine, and mixtures thereof.

26. A process for increasing the amount of creatine in the bloodstream of an animal, comprising the steps of preparing creatine acid sulfate, diluting said creatine acid sulfate to form an aqueous solution, and adding buffering and neutralizing agents, wherein said solution contains about 1.37% to about 2.06% by weight creatine acid sulfate and has a pH of about 7.2 to about 7.8, and administering said solution orally to an animal in an amount to supply a predetermined amount of creatine to said animal.

27. The process of claim 26, wherein said aqueous solution is substantially free of creatinine and is stable at room temperature for at least about 6 months.

28. The process of claim 26, wherein said buffering agent is tribasic potassium phosphate.

29. The process of claim 26, wherein said tribasic potassium phosphate is added in an effective amount to provide a source of phosphate loading.

30. The process of claim 26, wherein said creatine acid sulfate is prepared by forming an aqueous solution containing about 31% to about 35% by weight sulfuric acid and adding a creatine source in a stoichiometric amount to said solution having a pH of about 2–3, and immediately thereafter diluting with water and neutralizing the solution.

31. The process of claim 30, wherein said creatine source is creatine monohydrate.

32. The process of claim 26, wherein said aqueous solution further comprises at least one compound selected from the group consisting of pyruvic acid, pyruvate salts, and mixtures thereof.

33. The process of claim 26, wherein said aqueous solution further comprises at least one compound selected from the group consisting of glycine, arginine and methionine, and mixtures thereof.

34. The process of claim 26, wherein said aqueous solution further comprises about 8.0% to about 10.0% by weight glycerol.

35. A process of producing a creatine acid sulfate solution comprising the steps of forming an aqueous solution of sulfuric acid; and combining creatine monohydrate with said sulfuric acid solution in a molar ratio of about 2.0:1.0 to form a creatine acid sulfate reaction product having a pH of about 2–3, and thereafter immediately diluting and neutralizing said reaction product to avoid the formation of creatinine and to form an aqueous solution of creatine acid sulfate having a pH of less than about 7.8.

36. The process of claim 35, wherein said aqueous solution of sulfuric acid has a sulfuric acid concentration of about 31% to about 35% by weight.

37. The process of claim 35, further comprising the step of adding a tribasic potassium phosphate buffering and neutralizing agent to said aqueous creatine acid sulfate solution.

38. The process of claim 10, wherein said composition is produced by the steps of combining creatine monohydrate with an aqueous sulfuric acid solution in a creatine monohydrate to sulfuric acid molar ratio of about 2.0:1.0 to form a creatine acid sulfate reaction product having a pH of about 2–3, and thereafter immediately diluting and neutralizing said reaction product with tribasic potassium phosphate to avoid the formation of creatinine to form an aqueous solution of creatine acid sulfate.

* * * * *